United States Patent
Schollenberger et al.

(10) Patent No.: US 11,065,133 B2
(45) Date of Patent: Jul. 20, 2021

(54) PROSTHESIS THAT CAN BE ACTUATED BY EXTERNAL FORCE

(71) Applicant: APPSOCIAL.ORG STIFTUNG, Zürich (CH)

(72) Inventors: Fabian Schollenberger, Forch (CH); Wilfried J. Elspass, Wiesendangen (CH); Lukas Lengacher, Dietlikon (CH); Tobias Moser, Laupen ZH (CH)

(73) Assignee: APPSOCIAL.ORG STIFTUNG, Zürich (CH)

(*) Notice: Subject to any disclaimer, the term of this patent is extended or adjusted under 35 U.S.C. 154(b) by 9 days.

(21) Appl. No.: 16/336,156

(22) PCT Filed: Sep. 20, 2017

(86) PCT No.: PCT/EP2017/073730
§ 371 (c)(1),
(2) Date: Mar. 25, 2019

(87) PCT Pub. No.: WO2018/054945
PCT Pub. Date: Mar. 29, 2018

(65) Prior Publication Data
US 2019/0240047 A1     Aug. 8, 2019

(30) Foreign Application Priority Data
Sep. 26, 2016  (CH) .................................. 01252/16

(51) Int. Cl.
*A61F 2/54* (2006.01)
*A61F 2/68* (2006.01)
(Continued)

(52) U.S. Cl.
CPC ................ *A61F 2/70* (2013.01); *A61F 2/583* (2013.01); *A61F 2/72* (2013.01); *A61F 2/80* (2013.01);
(Continued)

(58) Field of Classification Search
CPC . B25J 13/003; A61F 2/70; A61F 2/583; A61F 2/72; A61F 2002/704; A61F 2002/7635; A61F 2/68; A61F 2/54
See application file for complete search history.

(56) References Cited

U.S. PATENT DOCUMENTS

| 5,413,611 A | 5/1995 | Haslam, II et al. |
| 6,589,287 B2 | 7/2003 | Lundborg |
| (Continued) | | |

FOREIGN PATENT DOCUMENTS

| CN | 101849865 A | 10/2010 |
| WO | 9848740 A1 | 11/1998 |
| WO | 2013/038187 | 3/2013 |

OTHER PUBLICATIONS

English translation of International Preliminary Report on Patentability dated Mar. 26, 2019 with Written Opinion.
(Continued)

*Primary Examiner* — Bruce E Snow
(74) *Attorney, Agent, or Firm* — Paul D. Bianco; Stephen Bongini; Fleit Intellectual Property Law

(57) ABSTRACT

A prosthesis that can be actuated by external force includes a prosthesis shaft and an exoprosthesis with at least one prosthesis motor that can be activated by a prosthesis control device and a joint. The prosthesis control device includes a housing, a microcontroller and display device, so that a gripping process can be replicated by the prosthesis motor controllable by the prosthesis control device and parameters of the gripping process are displayed on a display, in which case recording and evaluation of the electromyography signals are dispensed with. The display displays the chosen parameters of an imminent gripping process and the prosthesis control device includes an input device by which a desired gripping force and/or gripping time can be actively set on the microcontroller before performance of the gripping process by a prosthesis wearer directly on the prosthesis control device and can be readjusted during the gripping process.

19 Claims, 3 Drawing Sheets

(51) Int. Cl.
- *A61F 2/70* (2006.01)
- *A61F 2/58* (2006.01)
- *A61F 2/76* (2006.01)
- *A61F 2/80* (2006.01)
- *A61F 2/72* (2006.01)
- *B25J 13/00* (2006.01)

(52) U.S. Cl.
CPC . *A61F 2002/689* (2013.01); *A61F 2002/6881* (2013.01); *A61F 2002/704* (2013.01); *A61F 2002/705* (2013.01); *A61F 2002/769* (2013.01); *A61F 2002/7635* (2013.01); *B25J 13/00* (2013.01)

(56) References Cited

U.S. PATENT DOCUMENTS

| | | |
|---|---|---|
| 2010/0198362 A1 | 8/2010 | Puchhammer |
| 2010/0274365 A1 | 10/2010 | Evans et al. |
| 2014/0277588 A1 | 9/2014 | Patt et al. |
| 2016/0089212 A1* | 3/2016 | Balicki .................. A61B 34/25 606/130 |
| 2016/0374833 A1* | 12/2016 | Dechev ..................... A61F 2/54 623/62 |
| 2018/0064563 A1* | 3/2018 | Gill ........................ A61F 2/583 |
| 2019/0125550 A1* | 5/2019 | Goldfarb ................. A61F 2/586 |

OTHER PUBLICATIONS

Nakamura Y et al: Clinical Application of an Electrical Powered Upper Limb Prosthesis with Sensory Feedback System to a Patient with Above Elbow Amputation and Brachial Plexus Injury. Biomechanics. Rehabilitation. Electrical Phenomena. Biomaterials. San Diego. Oct. 28-31, 1993; [Proceedings of the Annual International Conference of the Engineering in Medicine and Biology Society]. New York. IEEE. US. vol. 15. Part 03. Oct. 28, 1993 (Oct. 28, 1993). XP000452860.

International Search Report dated Jan. 4, 2018 for PCT/EP2017/073730 filed Sep. 20, 2017.

Written Opinion for PCT/EP2017/073730 filed Sep. 20, 2017.

* cited by examiner

PROSTHESIS THAT CAN BE ACTUATED BY EXTERNAL FORCE

TECHNICAL FIELD

The present invention describes a prosthesis that can be actuated by external force, comprising a prosthesis shaft and an exoprosthesis with at least one prosthesis motor operable by means of a prosthesis control device and a joint, in which the prosthesis control device includes a housing, a microcontroller arranged in it and display device so that a gripping process can be replicated by a prosthesis motor controllable by the prosthesis control device and parameters of the gripping process can be displayed by the display device, in which case recording and evaluation of electromyography signals are dispensed with.

STATE OF THE ART

Prostheses comprising a prosthesis shaft with an exoprosthesis in the form of a hand or foot prosthesis that can be actuated by external force are now preferred. A prosthesis control device is then connected to the exoprosthesis, by means of which at least one prosthesis motor is driven so that at least one joint on the exoprosthesis can be moved. In the case of a hand prosthesis the movement of at least one finger joint is replicated, through which a gripping movement is possible.

Since suitable electronic components are available and affordable and the most realistic possible replications of natural hand and foot movements are envisaged, prostheses are widely equipped with myoelectric capability for use of electromyography (EMG). Electrical muscle activity can be determined by EMG, from which control signals can be generated for the prosthesis control device. The at least one prosthesis motor of the exoprosthesis is controlled by surface electrodes on the skin in the area of the extremity stump of a prosthesis wearer. The muscle signals that can be picked up along the prosthesis shaft are detected with the prosthesis control device by means of sensors and converted to movements of the exoprosthesis.

In addition to increased technical demand for such myoelectrically controlled prostheses that can be actuated by external force, it is necessary that the prosthesis wearer train the control by means of myoelectric signals. Use of a prosthesis with EMG is therefore generally only possible with a learning process to control the prosthesis, which is often time-consuming. The algorithms for recognition of the user input are difficult to set up and are often not reproducible, so that control often poses problems if the prosthesis wearer, for example, sweats and/or the surface electrodes shift. In addition, when such prostheses have been worn over long period of time, the EMG signal can diminish markedly through fatigue of individual muscle parts.

In order to eliminate the known drawbacks of prostheses based on EMG signals increasingly more demanding proposals are being made, which further increases the complexity of this type of prosthesis. Additional sensors are often used, for example, in order to detect a gripping movement even more precisely. The prosthesis control device becomes even more demanding and the prostheses become even more expensive, which hampers the use of prostheses in third world countries.

For example, a method for control of an EMG prosthesis is described in WO2013038187, which enables the prosthesis wearer to train prosthesis movements even if the prosthesis is not ready for use. The exoprosthesis can be optionally moved with the recorded EMG signals or movement simulated in the computer, in which case a prosthesis wearer can train real movements through the latter. The prosthesis wearer can start predefined programs, for example, for different gripping processes, through the correct muscle signals via computer and execute them with the exoprosthesis. In addition to a number of EMG sensors, after programming of predefined programs and by using a corresponding prosthesis control device, gripping programs can run with computer support. However, this is connected with further increased technical expense. In addition, a prosthesis wearer can only have the prosthesis run stored programs controlled by his EMG signals, which is less flexible. The sensor mechanisms, actuators and electronics for controlling the described prosthesis are cost-intensive and very complex.

In order to create simplified and especially affordable prostheses that exhibit reproducible movements and motor controls, attempts are being made to configure the prosthesis control device and the prosthesis motor more simply and to dispense with EMG sensors and additional computer support. If one skilled in the art dispenses with EMG sensors, it is not clear how reproducible gripping movements that are simple to carry out can be performed. Fragile objects, in particular, generally can no longer be grasped with the rudimentary prostheses known to one skilled in the art, without sensor support.

SUMMARY OF THE INVENTION

One aspect of the disclosure relates to a simple cost-effective prosthesis that can be actuated by external force, which is operable without demanding training and requires few components. Reproducible, disturbance-free and reliable gripping of objects of different hardness, controlled by external force, is attainable with this prosthesis, in which evaluation of electromyography signals and gripping force sensors are dispensed with.

In an embodiment, the prosthesis control device of the prosthesis can be manipulated from the outside by a prosthesis wearer before and during the gripping movement, in which the gripping force and gripping time can be simply and reliably set by the prosthesis wearer and also regulated during the gripping movement in real time by the prosthesis wearer. Among other things, the set gripping force and gripping time are reported to the prosthesis wearer optically, haptically and/or acoustically.

BRIEF DESCRIPTION OF THE DRAWINGS

A preferred practical example of the object of the invention is described below in conjunction with the appended drawings.

FIG. 1a shows a top view of a prosthesis with a prosthesis control device on an arm band positioned around the prosthesis shaft with enlargement of the display device in the form of a screen, whereas

FIG. 4 shows an exploded view of a prosthesis control device alone, whereas

DESCRIPTION

Figure 1A:
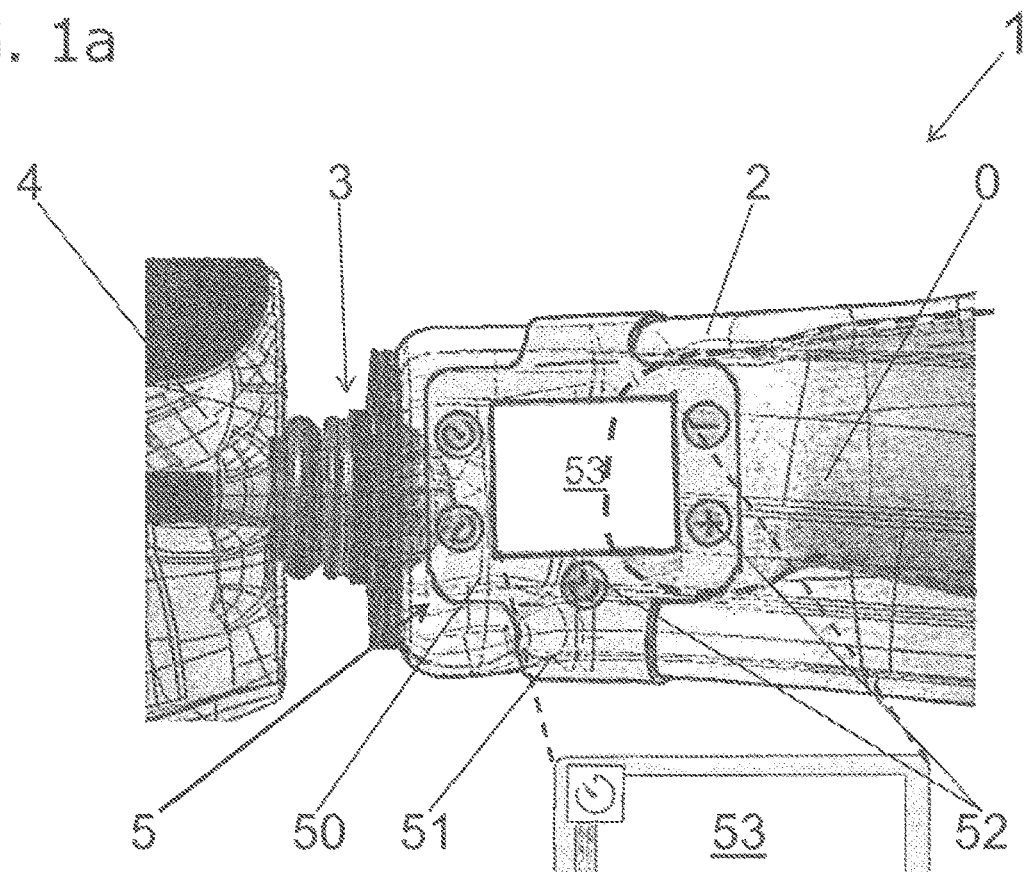

A prosthesis 1 controlled by external force, comprising a prosthesis shaft 2, a coupling 3, an exoprosthesis 4 and a prosthesis control device 5 is shown and explained here with respect to the example of a hand prosthesis. The prosthesis shaft 2 here is pushed over and releasably fastened to an extremity stump 0 in the form of a forearm stump 0, indicated with dashed lines. The hand prosthesis 4 is connected to the prosthesis shaft 2 by means of coupling 3. At least one motor-driven joint is situated on a hand prosthesis 4, by means of which gripping of an object can be accomplished. A prosthesis motor is not shown here but is designed so that it can be controlled by the prosthesis control device 5 through which a gripping process is formed.

The prosthesis control device 5 has a housing 50. The housing 50 is fastened to an arm band 51 positioned around the prosthesis shaft 2 so that the prosthesis control device 5 can be designed in the form of a wristwatch (FIG. 1a) or sports arm band (FIG. 1b).

For facilitated operation, the prosthesis control device 5 is fastened on the outer surface of the prosthesis shaft 2 and at a distance from the skin of the prosthesis wearer. This is readily possible, since no myoelectric signals are recorded by the prosthesis control device 5.

The prosthesis control device 5 and housing 50 have input device 52 and display device 53. The input device 52 can consist of virtual input buttons arranged on an operating surface 520, in addition to conventional pressure switches, keys, rotary potentiometers, buttons or switches. The operating surface 520 of the prosthesis control device 5 is arranged protruding from an outer surface of the exoprosthesis 4, prosthesis shaft 2 or coupling 3 and is therefore readily accessible. All input devices 52 are mechanically operable by a prosthesis wearer manually, i.e., with a finger. Operation preferably occurs with at least one finger of the intact hand but could also be operated by an aid held in the intact hand.

Figure 1B:
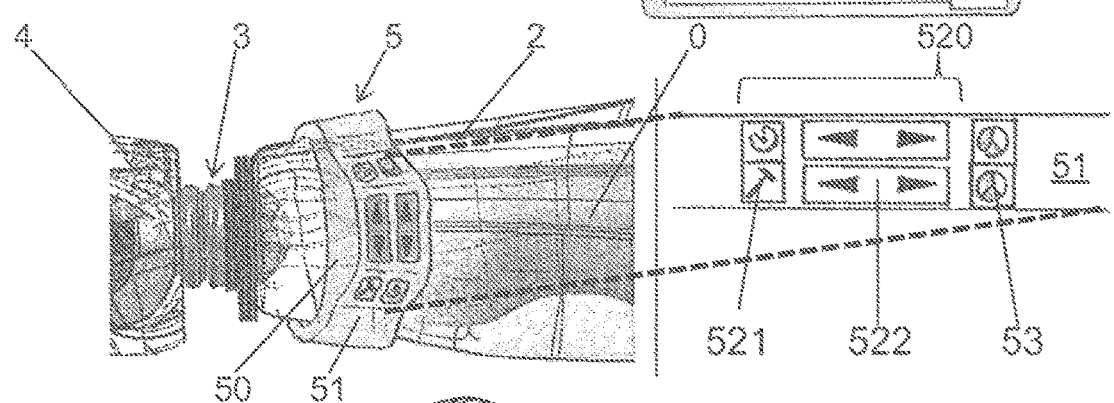
FIG. 1b shows a top view of a prosthesis with a prosthesis control device in the form of a sports arm band fastened on the prosthesis shaft.
Figure 2:
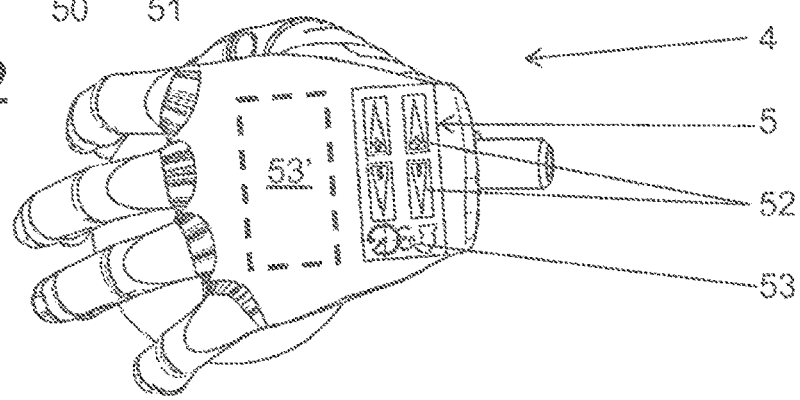
FIG. 2 shows a perspective view of a hand prosthesis after disconnection from the prosthesis shaft with a prosthesis control device integrated therein.

A screen is shown in FIG. 1a as a display device 53 with a display surface, whereas the input device 52 involves keys in addition to screen 53.

The prosthesis control device 5 permits display of the actual gripping force and gripping time on screen 53, so that a prosthesis wearer can easily read the parameters with which the next gripping movement must occur. The display device 53 can optically follow how the gripping movement will occur or is occurring.

The prosthesis control device 5 on prosthesis shaft 2, as shown in FIG. 1b, has a housing 50 with an arm band 51 in the form of a sports arm band or fitness arm band. The prosthesis wearer can enter parameters in the prosthesis control device 5 via keys 52, which can also be designed as capacitive or resistive switches 52 or pressure elements. Selection keys 521 are provided as input device 52, with which a mode or parameter to be set can be entered. In order to set the magnitude of the selected parameter, for example, the gripping force, size selection keys 522 are provided. The display device 53 used here can be LEDs in the simple case. The number of lit LEDs or the color of the lit LEDs can then optically indicate the set parameter, like gripping force or gripping time.

In another modification the prosthesis control device 5 is integrated into the exoprosthesis 4 so that a prosthesis wearer can perform parameter setting and reading of the values directly on the hand prosthesis 4. The housing 50 is integrated accordingly into the exoprosthesis 4 or part of the hand prosthesis 4 and forms the housing 50 of the prosthesis control device 5. The input device 52 and the display device 53 and optional display device 53' are situated directly on the exoprosthesis 4.

Figure 3:
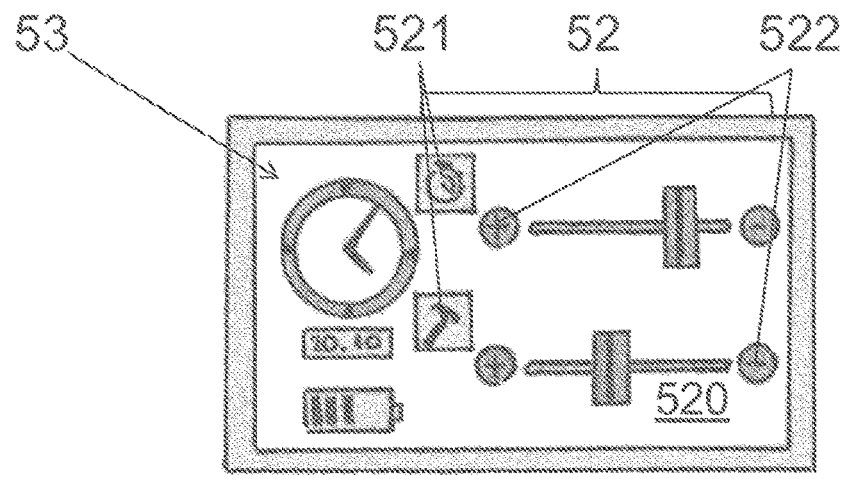
FIG. 3 shows a schematic view of a touch display as input and display device, which can be fastened on the prosthesis shaft or the hand prosthesis.

The display device 53 can also be configured as a touch-sensitive screen, as shown in FIG. 3. An operating software (firmware) or application (app) is preferably run on the prosthesis control device 5, which controls and displays the display 53 in the input device 52. An operating surface 50 can be provided as input device 52 on the touch-sensitive screen. The operating surface 520 includes input device 52 in the form of virtual selection keys 521 and virtual size selection keys 522 in the form of slide controls. During use of a touch-sensitive screen and an app, multiple results are attainable, the display device 53 and the input device 52 being provided on the touch-sensitive screen.

Since the prosthesis control device 5 preferably includes a single board computer, for example, an Arduino board or a Raspberry Pi, the prosthesis control device 5 can also be used for operation of additional apps, in addition to control of the exoprosthesis, as is known from smartphones and smartwatches. In addition to controlling the prosthesis that can be actuated by external force, the prosthesis wearer can therefore also run apps for music or video playback, game applications, messaging, or even telephone. A multiprocess operation is then naturally important, the prosthesis control always having priority over the other functions.

Figure 4:
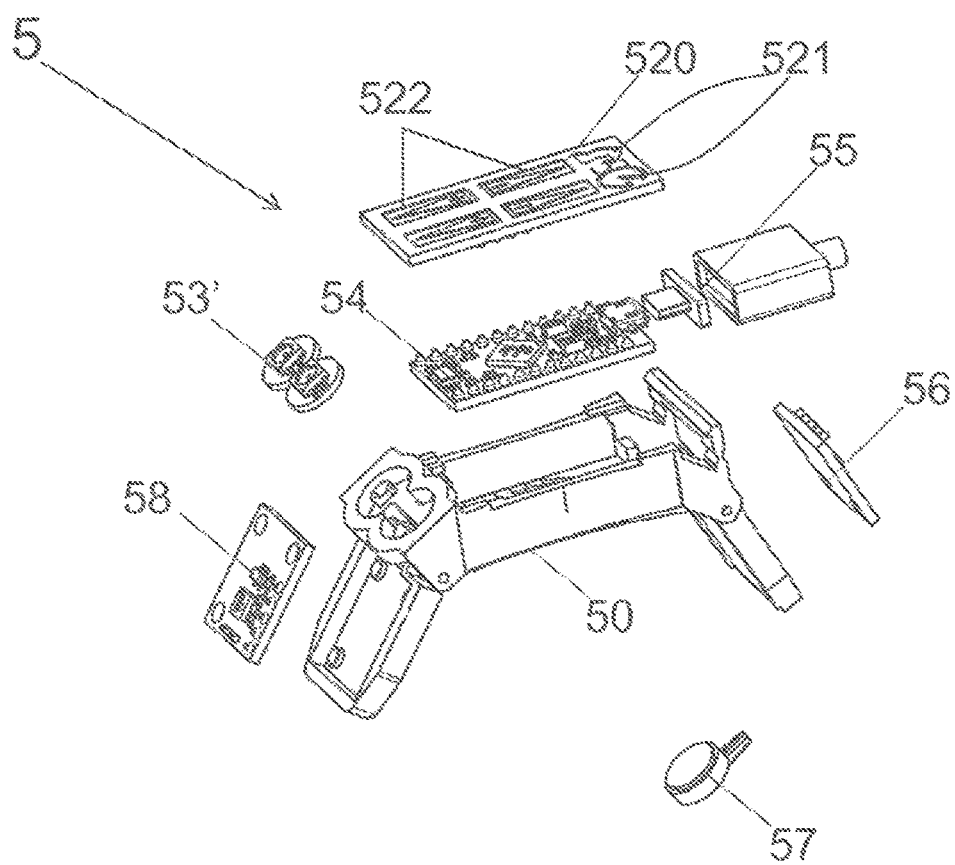

A prosthesis control device 5 is shown in detail in FIG. 4. A microcontroller 54 is mounted in the housing 50 as main part of the prosthesis control device 5, connected to a power supply 55. The power supply 55 is formed as a battery or one or more button batteries. An operating surface 520 represents the input device 54 and LEDs 53' represent the display device 53. The currently set parameters are displayed optically by means of LEDs 53' via the microcontroller 54 after input of the parameters. A haptic motor driver 56 and a vibration motor 57 are also connected to microcontroller 54. Initiated by microcontroller 54, the vibration motor 57 executes vibrations that the prosthesis wearer can feel when the prosthesis control device 5 is arranged on the prosthesis shaft 2 or directly on the hand prosthesis 4. Through the haptic motor driver 56 in conjunction with vibration motor 57 it is possible for the prosthesis wearer to recognize the gripping contact of the hand prosthesis 4 by vibrations. The objective is to also report through tactile sensation the set parameters to the prosthesis wearer, in which case a vibration can occur as soon as the gripping movement occurs with the set gripping force or if an object was grasped.

The operating surface 520 is designed here as a touch-sensitive PCB component (printed circuit on a circuit board), in which input occurs on the touch surfaces (touch pads). Selected parameters can be enlarged or reduced on the size selection keys 522, displayed as arrow-shaped surfaces. The parameters to be set can be varied by means of selection keys 521. The values entered on the operating surface 520 are sent to the microcontroller for further processing.

An acceleration sensor that is also connected to microcontroller 54 can optionally be integrated into the prosthesis control device 5. The movements and accelerations of the prosthesis control device 5 carried on the prosthesis shaft 2 and/or the exoprosthesis 4 can be recorded by the acceleration sensor 58.

The prosthesis control device 5 controls a gripping process by means of microcontroller 54, on which an operating software runs. Parameters are sent from the operating surface 520 to the microcontroller 54 through input device 52, processed by microcontroller 54 and displayed with display device 53. Controlled by the microcontroller 54, the prosthesis motor movement is controlled as set. Readjustment of the parameters by input device 52 by the prosthesis wearer is also possible in real time during the gripping process.

Figure 5:
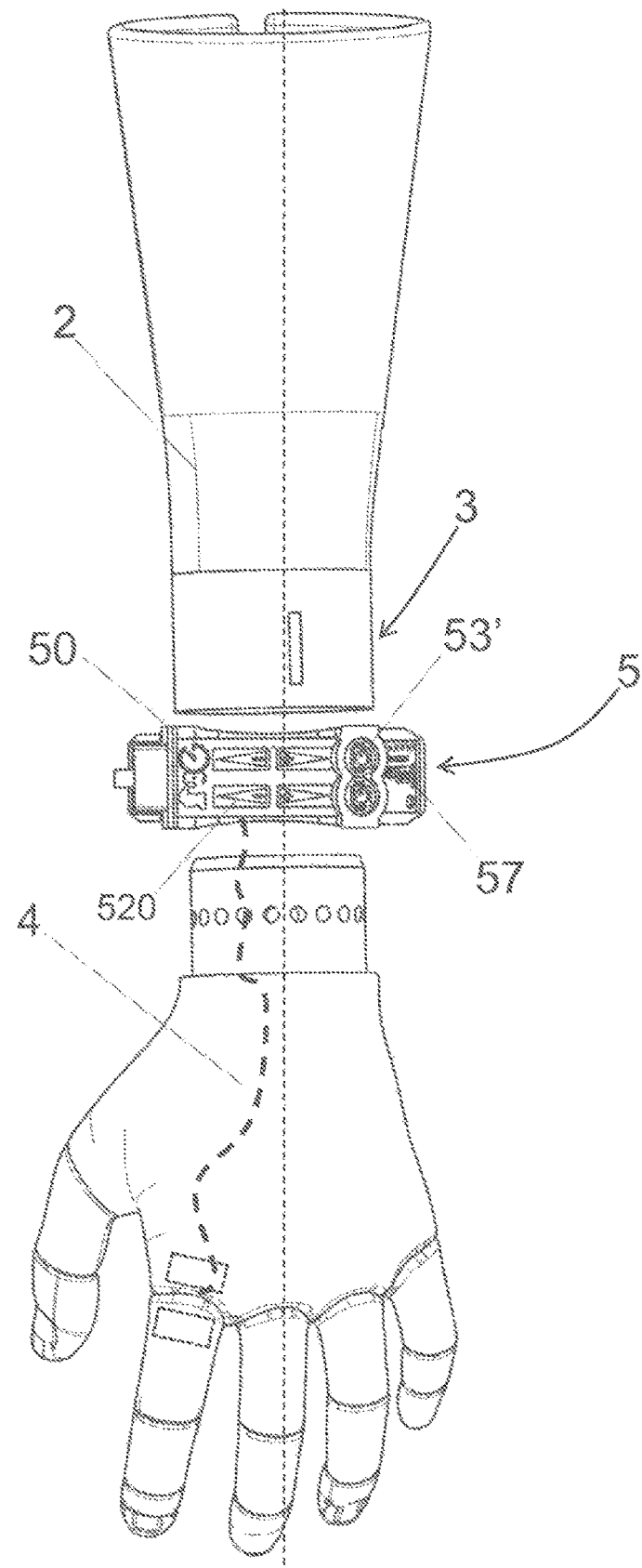
FIG. 5 shows a perspective view of the prosthesis control device arranged between the prosthesis shaft and hand prosthesis.

The power supply 55 is arranged in the prosthesis shaft 2 on the exoprosthesis 4 but could also be positioned differently on the body of the prosthesis wearer, for example, in a pants' pocket. As shown in FIG. 5, the prosthesis control device 5 can be arranged at least partially covering the coupling 3 between prosthesis shaft 3 and exoprosthesis 4. A connection of the prosthesis control device 5 to at least one finger joint of the hand prosthesis 4 is sketched here, which is movable by the prosthesis control device 5. A prosthesis motor, which can perform the gripping movement, is shown in a dashed line. The connection between prosthesis control device 5 and hand prosthesis 4 and the at least one prosthesis motor can occur through a cable or wirelessly, for example, by Bluetooth.

Control of the at least one prosthesis motor occurs through the prosthesis control device 5 after input of the parameters, especially the gripping time and gripping force. The at least one prosthesis motor is driven in controlled fashion by the microcontroller 54, in which case the parameters can also be changed in real time during the gripping process.

Method of Operation

Control and display of the gripping force and gripping time of the hand prostheses 4 actuated by external force occurs here with the described prosthesis control device 5.

During operation the prosthesis wearer will manually set on the operating surface 520 the gripping force to be achieved and possibly a gripping time before a movement of the hand prosthesis 4 or at least one joint of the hand prosthesis 4 can be carried out by means of the at least one prosthesis motor. This setting occurs with a finger of the intact hand, in which the parameter is chosen with selection keys 521 and the size with the size selection keys 522. The display device 53 indicates to the prosthesis wearer whether the desired settings are made. The settings are sent from the input device 52 to the microcontroller 54, which controls the output device 53 and movement of the hand prosthesis 4.

After setting of the desired parameters, the desired movement begins, which can be initiated, for example, by a defined position of the hand prosthesis relative to prosthesis shaft 2.

In the case of a gripping movement, the prosthesis wearer follows the movement himself, but also acquires tactile feedback, for example, concerning the beginning and end of the gripping movement, by means of vibrations. The display device 53 also shows the movement parameters and/or the trend of the movement optically. Control of the at least one prosthesis motor based on previously entered parameters occurs, initiated and controlled by the microcontroller 54.

If the process wearer recognizes that the gripping movement does not correspond to his wishes, he has the possibility during movement of a hand prosthesis 4 to change the parameters in real time via the operating surface 520. The prosthesis wearer can also manually alter the parameters again. Adapted target values, for example, the gripping force, are then sent to the microcontroller 54. The microcontroller 54 then controls the at least one prosthesis motor accordingly in altered form. An infinite time interval or a specific time interval less than infinite is considered as gripping time. Through the possibility of subsequent changing of the parameters, the gripping movement can be ended at any time, in which case the prosthesis motor releases the grip and opens the joint.

With the prosthesis control device 5 the prosthesis wearer can deliberately assign the gripping force of the hand prosthesis 4 at any time via an externally wearable module. Before an object is grasped, start parameters can be assigned before initiation by the prosthesis wearer. If during the gripping movement it is recognized that the gripping force was chosen too high, since the objects being gripped are softer than thought, the gripping force can be simply readjusted. Destruction of the gripped object can thus be ruled out.

Through tactile feedback by means of vibration motor 57, it can be indicated, for example, when the object being gripped is touched, grasped and released again. The gripping process can then approximate natural gripping.

The parameters and feedback signals set on the prosthesis control device 5 during movement can also be sent in the form of acoustic feedback instead of optical and haptic signals. At least one loudspeaker and an acoustic module is connected accordingly to microcontroller 54, from which acoustic feedback signals can be sent to the prosthesis wearer. The software operated on the microcontroller 54 can therefore acoustically report the sent gripping force or the successful conclusion of a gripping movement.

In another embodiment the prosthesis control device 5 can be designed in several parts, in which the input device 52 and the display device 53 are not arranged at the location of housing 50 but are spatially separated from each other.

As an alternative, the input device 52 could be designed in the form of an acoustic model connected to microcontroller 54, in which spoken commands received by the acoustic module can be used to input desired gripping force and/or gripping time on the microcontroller 54 of the prosthesis control device 5. The prosthesis wearer speaks before performance of a gripping process directly into the prosthesis control device 5 or the acoustic module and states the gripping force and/or gripping time. The understood voice command is then displayed by the display device 53 and gripping can be performed. A correspondingly voice-controlled prosthesis 1 will therefore be achieved.

Although the prosthesis control device 5 and the housing 50 is worn here as part of the prosthesis 1 on the extremity stump 0, the prosthesis control device can also be worn on the healthy or intact hand. Operation then occurs, for example, with a prosthesis finger when the input device 52 is configured in the form of manually operable keys.

LIST OF REFERENCE NUMBERS

0 Extremity stump/forearm stump
1 Prosthesis
2 Prosthesis shaft
3 Coupling for exoprosthesis
4 Exoprosthesis/hand prosthesis
5 Prosthesis control device
50 Housing
51 Arm band
52 Input device
520 Operating surface
521 Selection keys
522 Size selection keys
53 Display device (touch display, LEDs)
53' LEDs 54 Microcontroller
55 Power supply
56 Haptic motor driver
57 Vibration motor
58 Acceleration sensor 58

The invention claimed is:

1. A prosthesis comprising:
a prosthesis socket;
an exoprosthesis with a joint; and
at least one prosthesis motor that is activatable by a prosthesis control device, the joint of the exoprosthesis being movable by the prosthesis motor under control of the prosthesis control device so as to replicate a gripping process,
wherein the prosthesis control device includes a housing, a microcontroller arranged in the housing, and a display device for displaying parameters of the gripping process,
the prosthesis control device also includes an input device by which a desired gripping force and/or gripping time is actively settable by a prosthesis wearer directly on the prosthesis control device before performance of the gripping process, and is re-adjustable during the gripping process by the prosthesis wearer,
the desired gripping force and/or gripping time are displayable by the display device before performance of the gripping process, and
no electromyography signals are recorded or evaluated by the prosthesis control device.

2. The prosthesis according to claim 1, wherein the input device comprises selection keys and size selection keys on an operating surface, by which the settings occur on the prosthesis control device before performance of the gripping process by a prosthesis wearer directly on the prosthesis control device.

3. The prosthesis according to claim 2, wherein the input device is designed on the operating surface as capacitive or resistive switches or pressure elements that are mechanically activatable manually by the prosthesis wearer.

4. The prosthesis according to claim 2, wherein the operating surface is configured in the form of a touch-sensitive screen and the input device is chosen on the operating surface as virtual input buttons.

5. The prosthesis according to claim 2, wherein the operating surface is designed as a touch-sensitive PCB component in the form of a circuit board, in which the selection keys and the size selection keys are touch pads.

6. The prosthesis according to claim 2, wherein the display device is configured as representations on a touch-sensitive screen and the selection keys and the size selection keys are enterable on the touch-sensitive screen.

7. The prosthesis according to claim 1, wherein the display device comprises LEDs, the number of lit LEDs or the color of the lit LEDs optically indicating the parameters of the gripping process.

8. The prosthesis according to claim 1, wherein a vibration motor with a haptic motor driver is connected to the microcontroller so that the parameters and feedback signals of the gripping process are reported haptically to the prosthesis wearer.

9. The prosthesis according to claim 1,
wherein the microcontroller comprises a single board computer and an operating software for setting and display of the parameters of the gripping process and to control the gripping process, and
the microcontroller further comprises at least one application for music or video playback, for playing a game, for messaging, or for telephoning.

10. The prosthesis according to claim 1, wherein the housing is arranged integrated together with the microcontroller, the input device, and the display device in the exoprosthesis.

11. The prosthesis according to claim 1, wherein the housing is designed in the form of an arm band and is positioned around the prosthesis socket or a coupling between the prosthesis socket and the exoprosthesis.

12. The prosthesis according to claim 1, wherein connection between the prosthesis control device and the at least one prosthesis motor is wireless.

13. The prosthesis according to claim 1, wherein the desired gripping time is actively settable by the prosthesis wearer through the input device of the prosthesis control device.

14. The prosthesis according to claim 1, wherein the desired gripping force and/or gripping time is actively re-adjustable by the prosthesis wearer directly on the prosthesis control device during the gripping process.

15. The prosthesis according to claim 1, wherein the gripping process is initiateable by the prosthesis control device based on a defined position of the exoprosthesis relative to the prosthesis socket.

16. A prosthesis, comprising:
a prosthesis socket;
an exoprosthesis with a joint; and
at least one prosthesis motor that is activatable by a prosthesis control device, the joint of the exoprosthesis being movable by the prosthesis motor under control of the prosthesis control device so as to replicate a gripping process,
wherein the prosthesis control device includes a housing, and a microcontroller arranged in the housing,
the prosthesis control device also includes an input device by which a desired gripping force and/or gripping time is actively settable by a prosthesis wearer directly on the prosthesis control device before performance of the gripping process, and is re-adjustable during the gripping process by the prosthesis wearer,
at least one acoustic module and a loudspeaker are connected to the microcontroller of the prosthesis control device, an acoustic feedback of the desired gripping force and/or gripping time of the gripping process being sendable by the acoustic module and loudspeaker to the prosthesis wearer before and during performance of the gripping process, and
no electromyography signals are recorded or evaluated by the prosthesis control device.

17. The prosthesis according to claim 16, wherein the input device comprises the at least one acoustic module connected to the microcontroller so that voice commands by the prosthesis wearer are useable to actively set the desired gripping force and/or gripping time on the prosthesis control device before performance of the gripping process.

18. The prosthesis according to claim 16, wherein the housing is designed in the form of an arm band that is positionable around the prosthesis socket or a coupling between the prosthesis socket and the exoprosthesis.

19. The prosthesis according to claim 16,
wherein the microcontroller comprises a single board computer and software for setting the parameters of the gripping process and for controlling the gripping process, and the microcontroller further comprises at least one of a music playback application, a gaming application, a messaging application, and a telephoning application.

\* \* \* \* \*